United States Patent [19]

Wilson et al.

[11] Patent Number: 5,070,203

[45] Date of Patent: Dec. 3, 1991

[54] N,N'-SUBSTITUTEDBIS(PYRIDINIUM) SALTS

[75] Inventors: John C. Wilson; Peter S. Alexandrovich, both of Rochester, N.Y.

[73] Assignee: Eastman Kodak Company, Rochester, N.Y.

[21] Appl. No.: 560,939

[22] Filed: Jul. 31, 1990

[51] Int. Cl.$^5$ ................................................ C07F 5/02
[52] U.S. Cl. ........................................ 546/13; 430/110
[58] Field of Search ................... 546/13; 430/109, 110

[56] References Cited

U.S. PATENT DOCUMENTS 3,912,368 10/1975 Ponjee et al. ........................ 546/13
4,684,596 8/1987 Bonser et al. ....................... 430/110

OTHER PUBLICATIONS

Hackh "Chemical Dictionary", McGraw-Hall, 1983, p. 62.

Primary Examiner—C. Warren Ivy
Assistant Examiner—Celia Chang
Attorney, Agent, or Firm—Willard G. Montgomery

[57] ABSTRACT

New N,N'-substitutedbis(pyridinium) salts are provided having advantageous utility as charge agents in electrostatographic toners and developers. The salts have the structure:

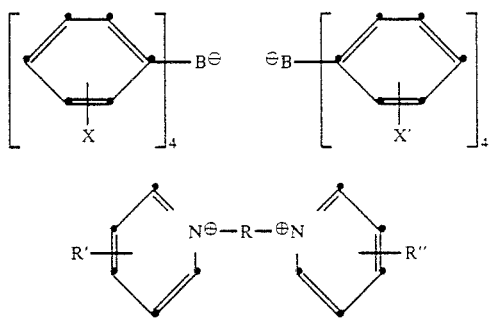

wherein R is alkylene having from 1 to 20 carbon atoms or arylenedialkylene wherein each alkylene moiety has 1 to 6 carbon atoms and the arylene moiety has from 6 to 14 carbon atoms, R' and R", which are the same or different, represent hydrogen, a straight or branched chain alkyl or alkoxy group having from 1 to 24 carbon atoms, aralkyl or alkaryl in which the alkyl group has 1 to 20 carbon atoms and the aryl group has from 6 to 14 carbon atoms, aryl having 6 to 14 carbon atoms which is unsubstituted or aryl having 6 to 14 carbon atoms which is substituted with one or more nitro, alkoxy or halo groups and X and X', which are the same or different, are chlorine, bromine, fluorine or iodine.

12 Claims, No Drawings

N,N'-SUBSTITUTEDBIS(PYRIDINIUM) SALTS

FIELD OF THE INVENTION

This invention relates to certain new N,N'-substitutedbis(pyridinium) salts which are useful as charge-control agents in dry electrostatographic toners and developers. More particularly, the new salts are thermally stable salts that can be well-dispersed in typical toner binder materials to form toners having good charging properties.

BACKGROUND OF THE INVENTION

In electrostatography an image comprising an electrostatic field pattern, usually of non-uniform strength, (also referred to as an electrostatic latent image) is formed on an insulative surface of an electrostatographic element by any of various methods. For example, the electrostatic latent image may be formed electrophotographically (i.e., by imagewise photo-induced dissipation of the strength of portions of an electrostatic field of uniform strength previously formed on a surface of an electrophotographic element comprising a photoconductive layer and an electrically conductive substrate), or it may be formed by dielectric recording (i.e., by direct electrical formation of an electrostatic field pattern on a surface of a dielectric material). Typically, the electrostatic latent image is then developed into a toner image by contacting the latent image with an electrostatographic developer. If desired, the latent image can be transferred to another surface before development.

One well-known type of electrostatographic developer comprises a dry mixture of toner particles and carrier particles. Developers of this type are commonly employed in well-known electrostatographic development processes such as cascade development and magnetic brush development. The particles in such developers are formulated such that the toner particles and carrier particles occupy different positions in the triboelectric continuum, so that when they contact each other during mixing to form the developer, they become triboelectrically charged, with the toner particles acquiring a charge of one polarity and the carrier particles acquiring a charge of the opposite polarity. These opposite charges attract each other such that the toner particles cling to the surfaces of the carrier particles. When the developer is brought into contact with the latent electrostatic image, the electrostatic forces of the latent image (sometimes in combination with an additional applied field) attract the toner particles, and the toner particles are pulled away from the carrier particles and become electrostatically attached imagewise to the latent image-bearing surface. The resultant toner image can then be fixed in place on the surface by application of heat or other known methods (depending upon the nature of the surface and of the toner image) or can be transferred to another surface, to which it then can be similarly fixed.

A number of requirements are implicit in such development schemes. Namely, the electrostatic attraction between the toner and carrier particles must be strong enough to keep the toner particles held to the surfaces of the carrier particles while the developer is being transported to and brought into contact with the latent image, but when that contact occurs, the electrostatic attraction between the toner particles and the latent image must be even stronger, so that the toner particles are thereby pulled away from the carrier particles and deposited on the latent image-bearing surface. In order to meet these requirements for proper development, the level of electrostatic charge on the toner particles should be maintained within an adequate range.

The toner particles in dry developers often contain material referred to as a charge agent or charge-control agent, which helps to establish and maintain toner charge within an acceptable range. Many types of charge-control agents have been used and are described in the published patent literature.

One general type of known charge-control agent comprises a quaternary ammonium salt. While many such salts are known, some do not perform an adequate charge-control function in any type of developer, some perform the function well in only certain kinds of developers, and some control charge well but produce adverse side effects.

A number of quaternary ammonium salt charge-control agents are described, for example, in U.S. Pat. Nos. 4,684,596; 4,394,430; 4,338,390; 4,490,455; and 4,139,483. Unfortunately, many of those known charge-control agents exhibit one or more drawbacks in some developers.

A particularly undesirable characteristic or property that some of the known quaternary ammonium salt charge agents possess is a lack of thermal stability and, thus, totally or partially decompose during attempts to mix them with known toner binder materials in well-known processes of preparing toners by mixing addenda with molten toner binders. Such processes are often referred to as melt-blending or melt-compounding processes and are commonly carried out at temperatures ranging from about 120° to about 200° C. Thus, charge agents that are thermally unstable at temperatures at or below 200° C. can exhibit this decomposition problem.

It would, therefore, be desirable to provide new salts that could perform the charge-controlling function well in dry electrographic toners and developers, while avoiding or minimizing the drawback noted above. The present invention does this.

SUMMARY OF THE INVENTION

The invention provides new N,N'-substitutedbis(pyridinium) salts having the structure

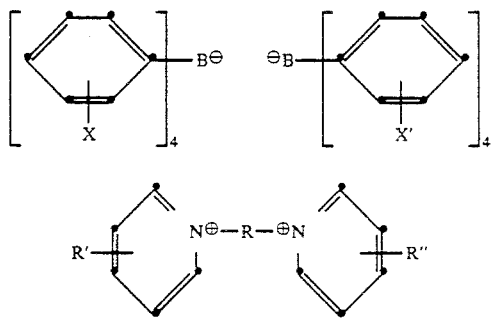

wherein R is alkylene having from 1 to 20 carbon atoms or arylenedialkylene wherein each alkylene moiety has 1 to 6 carbon atoms and the arylene moiety has from 6 to 14 carbon atoms, R' and R", which are the same or different, represent hydrogen, a straight or branched chain alkyl or alkoxy group having from 1 to 24 carbon atoms, aralkyl or alkaryl in which the alkyl group has 1 to 20 carbon atoms and the aryl group has from 6 to 14 carbon atoms, aryl having 6 to 14 carbon atoms which is unsubstituted or aryl having 6 to 14 carbon atoms which is substituted with one or more nitro, alkoxy or halo groups and X and X', which are the same or different, are chlorine, bromine, fluorine or iodine.

The salts of the invention have advantageous utility as charge agents in dry, particulate, electrostatographic toners and developers. Such toners comprise a polymeric binder and a charge-control agent chosen from the inventive salts defined above. Such developers comprise carrier particles and the particulate toner defined above.

The new salts of the invention provide good charge control in toners and developers. The inventive salts do not exhibit unacceptably high environmental sensitivity and have decomposition points well above 200° C.

DESCRIPTION OF THE PREFERRED EMBODIMENTS

The new N,N'-substitutedbis(pyridinium) salts of the invention can be conveniently prepared from readily available starting materials, such as a halide salt of an appropriate N,N'-substitutedbis(pyridinium) and an alkali metal salt of a tetraphenylborate. For example, N,N'-pentamethylenebis(pyridinium)dibromide, as an aqueous solution, when mixed with an aqueous solution of sodium tetraphenylborate in stoichiometric proportions spontaneously reacts to form a precipitate of the desired N,N'-pentamethylenebis(pyridinium) salt. The N,N'-substitutedbis(pyridinium) halide precursor may be prepared from the appropriate organic dihalide and pyridine in solution.

Illustrative examples of N,N'-substitutedbis(-pyridinium) salts useful in the present invention include, for example, N,N'-methylenebis(pyridinium) di(tetraphenylborate), N,N'-ethylenebis(pyridinium) di(tetraphenylborate), N,N'-pentamethylenebis(pyridinium) di(tetraphenylborate), N,N'-octamethylenebis(-pyridinium) di(tetraphenylborate), N,N'-pentamethylenebis(2-methylpyridinium) di(tetraphenylborate), 2-methyl-2'-ethyl-N,N'-ethylenebis(pyridinium) di(tetraphenylborate), N,N'-ethylenebis(2-methoxypyridinium) di(tetraphenylborate), N,N'-(p-xylene-α,α')bis(pyridinium) di(tetraphenylborate), N,N'-pentamethylenebis(pyridinium) di(tetra(4-chlorophenyl)borate), and N,N'-pentamethylenebis(4-benzylpyridinium) di(tetraphenylborate). A particularly useful N,N'-substitutedbis(pyridinium) salt is N,N'-pentamethylenebis(pyridinium) di(tetraphenylborate).

To be utilized as a charge-control agent in electrostatographic toners, the inventive N,N'-substitutedbis(-pyridinium) salt is mixed in any convenient manner (as, for example, by melt-blending as described in U.S. Pat. Nos. 4,684,596 and 4,394,430) with an appropriate polymeric toner binder material and any other desired addenda, and the mix is then ground to desired size to form a free-flowing powder of toner particles containing the charge agent. Other suitable methods of preparing electrostatographic toners comprising the charge-control agents of the present invention include those well known in the art such as spray drying, melt dispersion and dispersion polymerization.

Such toner particles can have an average diameter between about 0.1 μm and about 100 μm, a value in the range from about 1.0 to about 30 μm being preferable for many currently used machines. However, larger or smaller particles may be needed for particular methods of developement or development conditions.

Generally, it is desirable to add from about 0.05 to about 6 parts and preferably 0.05 to about 2.0 parts by weight of the aforementioned N,N'-substitutedbis(-pyridinium) salts per 100 parts by weight of a polymer to obtain an improved toner composition, although larger or smaller amounts of a charge control agent can be added, if desired. Of course, it must be recognized that the optimum amount of charge-control agent to be added will depend, in part, on the particular N,N'-substitutedbis(pyridinium) charge-control agent selected and the particular polymer to which it is added. However, the amounts specified hereinabove are typical of a useful range of charge-control agent which can be utilized in conventional dry toner materials.

The polymers useful as toner binders with the salts of the present invention can be used alone or in combination and include those polymers conventionally employed in electrostatic toners. Useful polymers generally have a glass transition temperature within the range of from 50° to 120° C. Preferably, toner particles prepared from these polymers have relatively high caking temperature, for example, higher than about 60° C., so that the toner powders can be stored for relatively long periods of time at fairly high temperatures without having individual particles agglomerate and clump together. The softening point of useful polymers preferably is within the range of from about 65° C. to about 200° C. so that the toner particles can readily be fused to a conventional paper receiving sheet to form a permanent image. Especially preferred polymers are those having a softening point within the range of from about 65° to about 120° C. Of course, where other types of receiving elements are used, for example, metal plates such as certain printing plates, polymers having a softening point and glass transition temperature higher than the values specified above can be used.

Among the various polymers which can be employed in toner particles with the salts of the present invention are polycarbonates, resin-modified maleic alkyd polymers, polyamides, phenol-formaldehyde polymers and various derivatives thereof, polyester condensates, modified alkyd polymers, aromatic polymers containing alternating methylene and aromatic units such as described in U.S. Pat. No. 3,809,554 and fusible cross-linked polymers as described in U.S. Pat. No. Re. 31,072.

Typical useful toner polymers include certain polycarbonates such as those described in U.S. Pat. No. 3,694,359, which include polycarbonate materials containing an alkylidene diarylene moiety in a recurring unit and having from 1 to about 10 carbon atoms in the alkyl moiety. Other useful polymers having the above-described physical properties include polymeric esters of acrylic and methacrylic acid such as poly(alkyl acrylate), and poly(alkyl methacrylate) wherein the alkyl moiety can contain from 1 to about 10 carbon atoms. Additionally, other polyesters having the aforementioned physical properties are also useful. Among such other useful polyesters are copolyesters prepared from terephthalic acid (including substituted terephthalic acid), a bis(hydroxyalkoxy)phenylalkane having from 1 to 4 carbon atoms in the alkoxy radical and from 1 to 10 carbon atoms in the alkane moiety (which can also be a halogen-substituted alkane), and an alkylene glycol having from 1 to 4 carbon atoms in the alkylene moiety.

Other useful polymers are various styrene-containing polymers. Such polymers can comprise, e.g., a polymerized blend of from about 50 to about 100 percent by weight of styrene, from 0 to about 45 percent by weight of a lower alkyl acrylate or methacrylate having from 1 to about 4 carbon atoms in the alkyl moiety such as methyl, ethyl, isopropyl, butyl, etc. and from about 5 to about 40 percent by weight of another vinyl monomer other than styrene, for example, a higher alkyl acrylate or methacrylate having from about 6 to 20 or more carbon atoms in the alkyl group. Typical styrene-containing polymers prepared from a copolymerized blend as described hereinabove are copolymers prepared from a monomeric blend of 40 to 60 percent by weight styrene or styrene homolog, from about 20 to about 50 percent by weight of a lower alkyl acrylate or methacrylate and from about 5 to about 30 percent by weight of a higher alkyl acrylate or methacrylate such as ethylhexyl acrylate (e.g., styrene-butyl acrylate-ethylhexyl acrylate copolymer). Preferred fusible styrene copolymers are those which are covalently crosslinked with a small amount of a divinyl compound such as divinylbenzene. A variety of other useful styrene-containing toner materials are disclosed in U.S. Pat. Nos. 2,918,460; Re 25,316; 2,788,288; 2,638,416; 2,618,552 and 2,659,670.

Various kinds of well-known addenda (e.g., colorants, release agents, etc.) can also be incorporated into toners containing salts of the invention.

Numerous colorant materials selected from dyestuffs or pigments can be employed in such toners. Such materials serve to color the toner and/or render it more visible. Of course, suitable toner materials having the appropriate charging characteristics can be prepared without the use of a colorant material where it is desired to have a developed image of low optical density. In those instances where it is desired to utilize a colorant, the colorants can, in principle, be selected from virtually any of the compounds mentioned in the Colour Index Volumes 1 and 2, Second Edition.

Included among the vast number of useful colorants are such materials as Hansa Yellow G (C.I. 11680), Nigrosine Spirit soluble (C.I. 50415), Chromogen Black ETOO (C.I. 45170), Solvent Black 3 (C.I. 26150), Fuchsine N (C.I. 42510), C.I. Basic Blue 9 (C.I. 52015). Carbon black also provides a useful colorant. The amount of colorant added may vary over a wide range, for example, from about 1 to about 20 percent of the weight of the polymer. Particularly good results are obtained when the amount is from about 1 to about 10 percent.

To be utilized as toners in electrostatographic developers, toners containing salts of this invention can be mixed with a carrier vehicle. The carrier vehicles which can be used to form such developer compositions can be selected from a variety of materials. Such materials include carrier core particles and core particles overcoated with a thin layer of film-forming resin.

The carrier core materials can comprise conductive, non-conductive, magnetic, or non-magnetic materials. For example, carrier cores can comprise glass beads; crystals of inorganic salts such as aluminum potassium chloride; other salts such as ammonium chloride or sodium nitrate; granular zircon; granular silicon; silicon dioxide; hard resin particles such as poly(methyl methacrylate); metallic materials such as iron, steel, nickel, carborundum, cobalt, oxidized iron; or mixtures or alloys of any of the foregoing. See, for example, U.S. Pat. Nos. 3,850,663 and 3,970,571. Especially useful in magnetic brush development schemes are iron particles such as porous iron particles having oxidized surfaces, steel particles, and other "hard" or "soft" ferromagnetic materials such as gamma ferric oxides or ferrites, such as ferrites of barium, strontium, lead, magnesium, or aluminum. See, for example, U.S. Pat. Nos. 4,042,518; 4,478,925; and 4,546,060.

As noted above, the carrier particles can be overcoated with a thin layer of a film-forming resin for the purpose of establishing the correct triboelectric relationship and charge level with the toner employed. Examples of suitable resins are the polymers described in U.S. Pat. Nos. 3,547,822; 3,632,512; 3,795,618 and 3,898,170 and Belgian Patent No. 797,132. Other useful resins are fluorocarbons such as polytetrafluoroethylene, poly(vinylidene fluoride), mixtures of these, and copolymers of vinylidene fluoride and tetrafluoroethylene. See, for example, U.S. Pat. Nos. 4,545,060; 4,478,925; 4,076,857; and 3,970,571. Such polymeric fluorohydrocarbon carrier coatings can serve a number of known purposes. One such purpose can be to aid the developer to meet the electrostatic force requirements mentioned above by shifting the carrier particles to a position in the triboelectric series different from that of the uncoated carrier core material, in order to adjust the degree of triboelectric charging of both the carrier and toner particles. Another purpose can be to reduce the frictional characteristics of the carrier particles in order to improve developer flow properties. Still another purpose can be to reduce the surface hardness of the carrier particles so that they are less likely to break apart during use and less likely to abrade surfaces (e.g., photoconductive element surfaces) that they contact during use. Yet another purpose can be to reduce the tendency of toner material or other developer additives to become undesirably permanently adhered to carrier surfaces during developer use (often referred to as scumming). A further purpose can be to alter the electrical resistance of the carrier particles.

A typical developer composition containing the above-described toner and a carrier vehicle generally comprises from about 1 to about 20 percent by weight of particulate toner particles and from about 80 to about 99 percent by weight carrier particles. Usually, the carrier particles are larger than the toner particles. Conventional carrier particles have a particle size on the order of from about 20 to about 1200 microns, preferably 30–300 microns.

Alternatively, toners containing salts of the present invention can be used in a single component developer, i.e., with no carrier particles.

Toner and developer compositions containing salts of this invention can be used in a variety of ways to develop electrostatic charge patterns or latent images. Such developable charge patterns can be prepared by a number of means and be carried for example, on a light sensitive photoconductive element or a non-light-sensitive dielectric-surfaces element such as an insulator-coated conductive sheet. One suitable development technique involves cascading the developer composition across the electrostatic charge pattern, while another technique involves applying toner particles from a magnetic brush. This latter technique involves the use of a magnetically attractable carrier vehicle in forming the developer composition. After imagewise deposition of the toner particles, the image can be fixed, e.g., by heating the toner to cause it to fuse to the substrate carrying the toner. If desired, the unfused image can be transferred to a receiver such as a blank sheet of copy paper and then fused to form a permanent image.

The following examples are presented to further illustrate some preferred embodiments of the salts of the invention and to compare their properties and performance to those of salts outside the scope of the invention.

EXAMPLE 1

PREPARATION OF N,N'-PENTAMETHYLENEBIS(PYRIDINIUM) DI(TETRAPHENYLBORATE)

A solution of 68.45 g (0.20 mol) of sodium tetraphenylborate in 700 mL of water was added to a solution of 38.8 (0.10 mol) N,N'-pentamethylenebis(-pyridinium) dibromide in 400 mL of water. The mixture was stirred for 30 minutes, filtered, and the collected solid was washed with water and methanol. The solid was recrystallized from acetonitrile, collected and dried to give 56.0 g (64.6%) of N,N'-pentamethylenebis(-pyridinium) di(tetraphenylborate); mp=228°–230° C. $^1$H NMR was consistent with the proposed structure. Atomic analysis calculated for $C_{63}H_{60}B_2N_2$ (866.82): 87.3% C, 7.0% H, 2.5% B, 3.2% N. Found: 87.7% C, 7.0% H, 2.6% B, 3.2% N.

The other salts within the scope of the invention are prepared similarly.

EXAMPLE 2

SALT DECOMPOSITION POINT

The N,N'-alkylenebis(pyridinium) salt of Example 1 was compared to quaternary ammonium salts outside the scope of the present invention in regard to decomposition point. Decomposition temperatures were determined by thermal gravimetric analysis (TGA) measured on a DuPont 1090 thermal analyzer equipped with a 951 thermal gravimetric analyzer (10° C./min; air). A sample of known weight is placed in the thermal analyzer and its weight is monitored while the temperature is raised at a constant rate, in this case 10° C./min. The temperature at which significant weight loss begins to occur is taken as the decomposition temperature. Results are presented in Table 1.

TABLE 1

| Salt | Of the Invention | Decomposition Point (°C.) |
|---|---|---|
| N,N'-pentamethylene-bis(pyridinium) di(tetraphenylborate) | Yes | 278 |
| N-benzyl-N,N-dimethylocta-decylammonium chloride | No | 160 |
| N-(p-nitrobenzyl)-N,N-dimethyloctadecyl-ammonium chloride | No | 189 |

The data in Table 1 shows that the inventive salts have a decomposition point well above 200° C., whereas the non-inventive salts have a decomposition point below 200° C. indicating likely decomposition of the latter during some toner melt-blending processes.

The invention has been described in detail with particular reference to preferred embodiments thereof, but it will be understood that variations and modifications can be effected within the spirit and scope of the invention.

We claim:

1. An N,N'-substitutedbis(pyridinium) salt having the structure

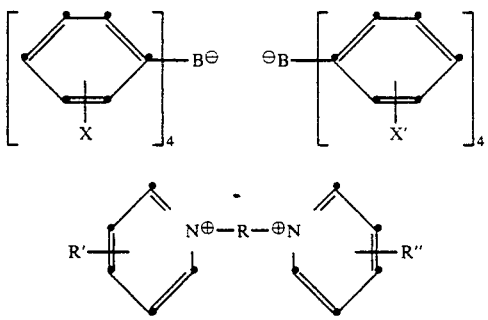

wherein R is alkylene having from 1 to 20 carbon atoms or arylenedialkylene wherein each alkylene moiety has 1 to 6 carbon atoms and the arylene moiety has from 6 to 14 carbon atoms, R' and R'', which are the same or different, represent hydrogen, a straight or branched chain alkyl or alkoxy group having from 1 to 24 carbon atoms, aralkyl or alkaryl in which the alkyl group has 1 to 20 carbon atoms and the aryl group has from 6 to 14 carbon atoms, aryl having 6 to 14 carbon atoms which is unsubstituted or aryl having 6 to 14 carbon atoms which is substituted with one or more nitro, alkoxy or halo groups and X and X', which are the same or different, are chlorine, bromine, fluorine or iodine.

2. The salt of claim 1, wherein said salt is N,N'-methylenebis(pyridinium) di(tetraphenylborate).

3. The salt of claim 1, wherein said salt is N,N'-ethylenebis(pyridinium) di(tetraphenylborate).

4. The salt of claim 1, wherein said salt is N,N'-pentamethylenebis(pyridinium) di(tetraphenylborate).

5. The salt of claim 1, wherein said salt is N,N'-octamethylenebis(pyridinium) di(tetraphenylborate).

6. The salt of claim 1, wherein said salt is N,N'-pentamethylenebis(2-methylpyridinium) di(tetraphenylborate).

7. The salt of claim 1, wherein said salt is 2-methyl-2'-ethyl-N,N'-ethylenebis(pyridinium) di(tetraphenylborate).

8. The salt of claim 1, wherein said salt is N,N'-ethylenebis(2-methoxypyridinium) di(tetraphenylborate).

9. The salt of claim 1, wherein said salt is N,N'-(p-xylene-α,α')bis(pyridinium) di(tetraphenylborate).

10. The salt of claim 1, wherein said salt is N,N'-pentamethylenebis(pyridinium) di(tetra(4-chlorophenyl)borate).

11. The salt of claim 1, wherein said salt is N,N'-pentamethylenebis(2-methylpyridinium) di(tetraphenylborate)

12. The salt of claim 1, wherein said salt is N,N'-pentamethylenebis(4-benzylpyridinium) di(tetraphenylborate).

* * * * *